(12) United States Patent
Leedom et al.

(10) Patent No.: US 6,237,590 B1
(45) Date of Patent: *May 29, 2001

(54) DRY POWDER DELIVERY SYSTEM APPARATUS

(75) Inventors: Marvin Allan Leedom, Princeton; Allan Eugene White, Hightstown, both of NJ (US)

(73) Assignee: Delsys Pharmaceutical Corporation, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/932,489

(22) Filed: Sep. 18, 1997

(51) Int. Cl.[7] .......................... A61M 15/00; A61M 15/08
(52) U.S. Cl. ................. 128/203.15; 128/203.12; 128/203.23
(58) Field of Search ............... 128/315, 203.12, 128/203.21, 203.23, 205.15, 203.18, 203.14, 203.19, 203.24

(56) References Cited

U.S. PATENT DOCUMENTS

| | | | |
|---|---|---|---|
| 3,967,761 | * 7/1976 | Melton, Jr. et al. | 128/203.15 |
| 4,294,361 | * 10/1981 | Margulies et al. | 206/532 |
| 4,604,847 | * 8/1986 | Moulding, Jr. et al. | 53/75 |
| 4,979,149 | 12/1990 | Popovic et al. . | |
| 5,042,472 | * 8/1991 | Bunin | 128/203.15 |
| 5,447,151 | * 9/1995 | Bruna et al. | 128/203.15 |
| 5,474,059 | * 12/1995 | Cooper | 128/203.12 |
| 5,492,112 | * 2/1996 | Mecikalski et al. | 128/203.15 |
| 5,497,763 | * 3/1996 | Lloyd et al. | 128/200.14 |
| 5,619,984 | 4/1997 | Hodson et al. . | |
| 5,622,166 | * 4/1997 | Eisele et al. | 128/203.12 |
| 5,669,973 | * 9/1997 | Pletcher | 118/624 |
| 5,694,920 | * 12/1997 | Abrams et al. | 128/200.16 |
| 5,769,073 | * 6/1998 | Eason et al. | 128/203.15 |
| 5,855,564 | * 1/1999 | Ruskewicz | 604/62 |
| 5,857,456 | * 1/1999 | Sun et al. | 128/203.15 |
| 5,896,855 | * 4/1999 | Hobbs et al. | 128/203.12 |
| 5,906,202 | * 5/1999 | Schuster et al. | 128/203.12 |

* cited by examiner

*Primary Examiner*—John G. Weiss
*Assistant Examiner*—Todd M. Martin
(74) *Attorney, Agent, or Firm*—Elliott M. Olstein; William Squire

(57) ABSTRACT

Provided is a powder delivery system which uses mechanical or electrical means to individually release covers that cover powder at a variety of powder aliquot locations on a rigid substrate.

23 Claims, 5 Drawing Sheets

DRY POWDER DELIVERY SYSTEM APPARATUS

Figure 1:
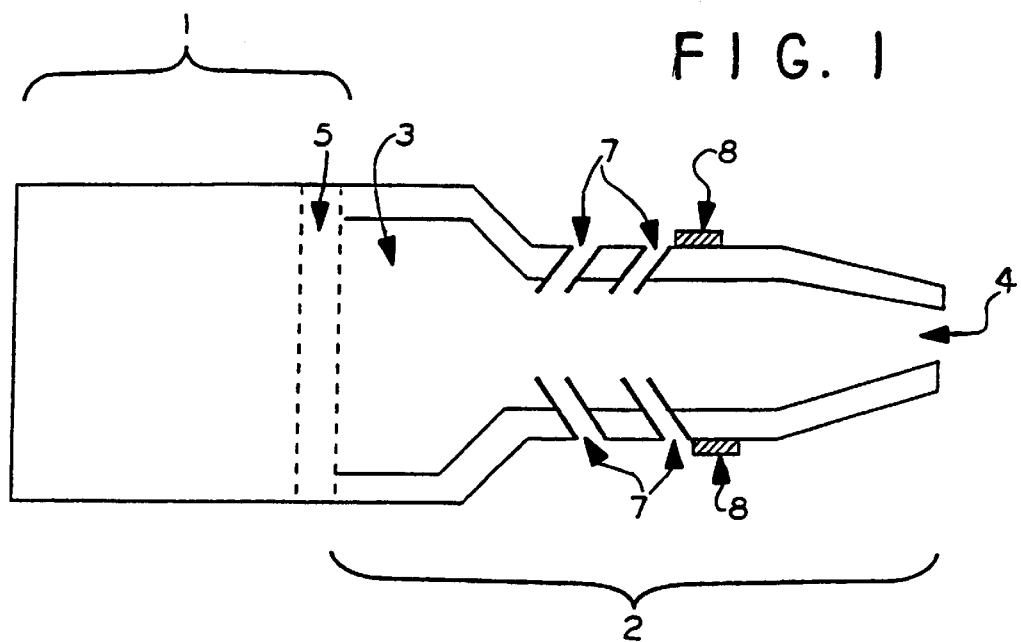
Figure 2A:
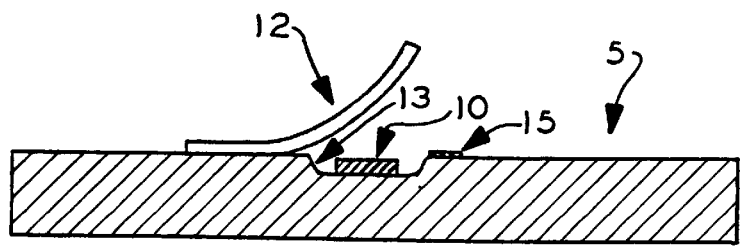
Figure 2B:
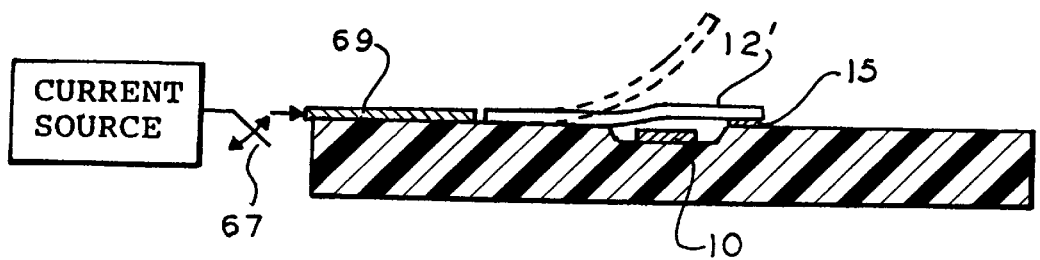
Figure 3A:
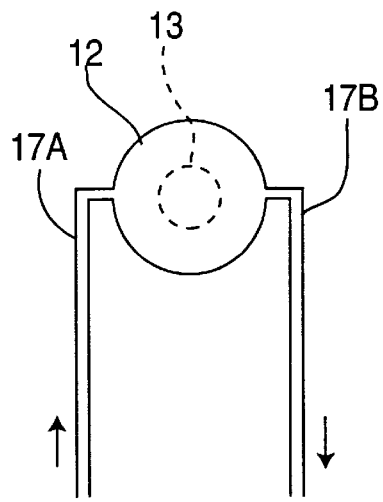
Figure 3B:
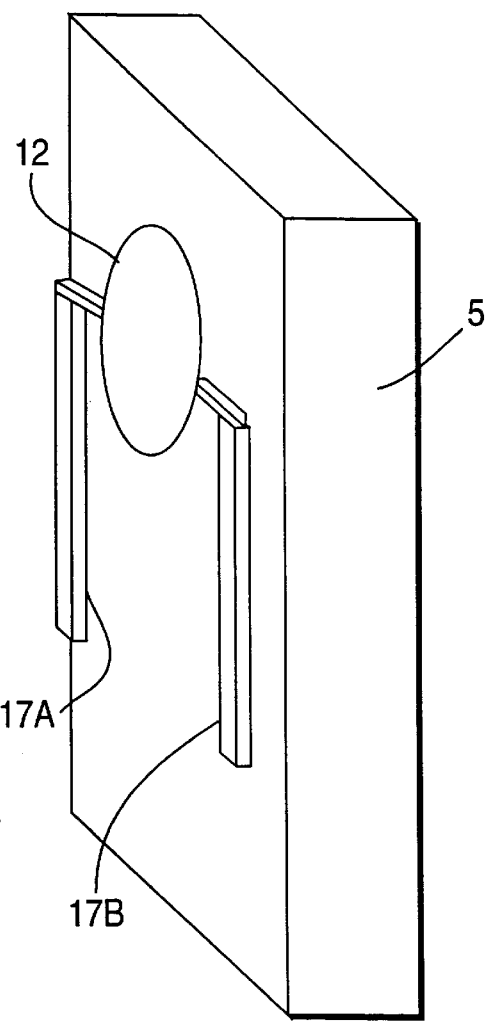
Figure 3D:
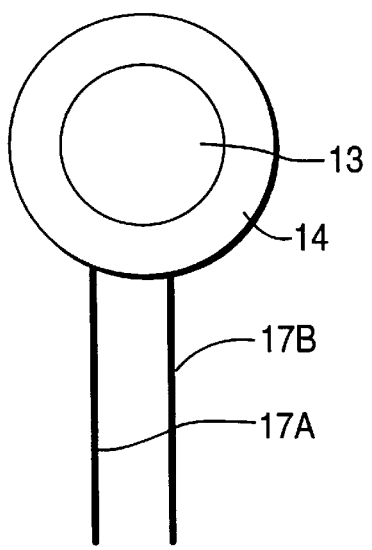
Figure 3C:
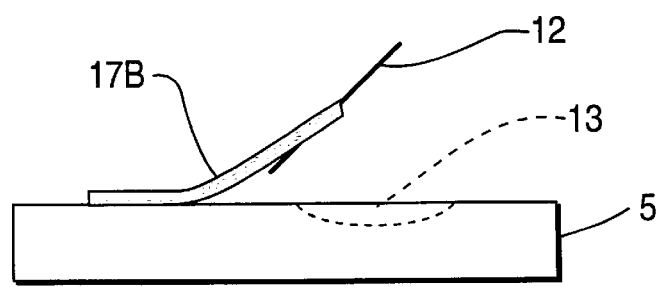
Figure 4:
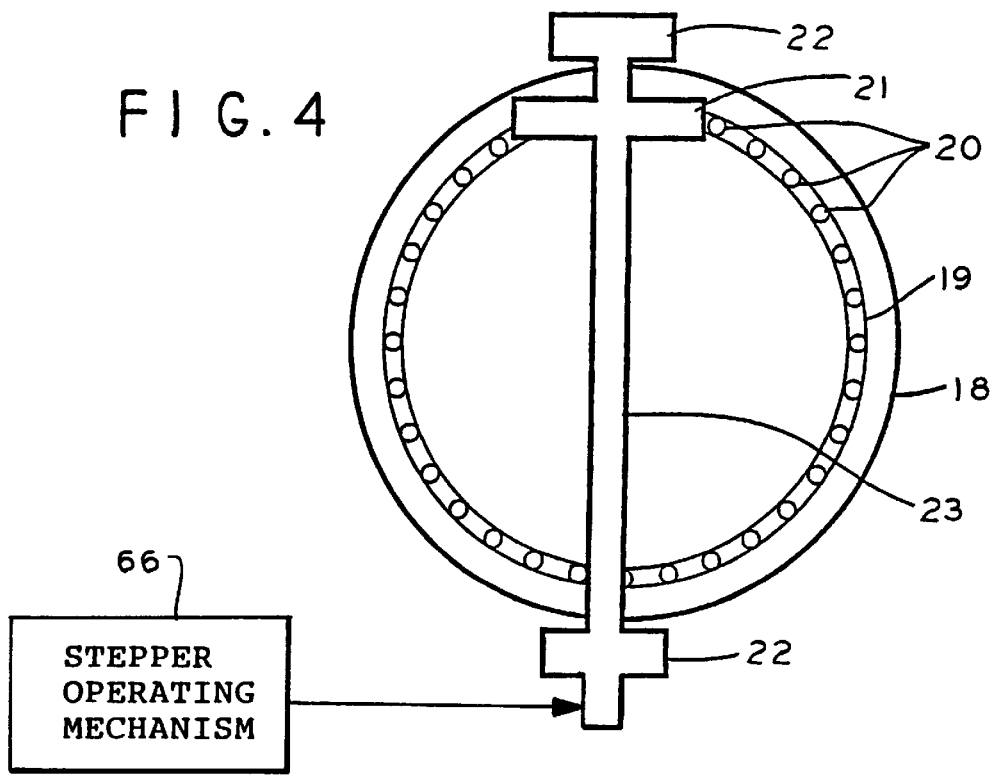

The invention relates to systems for delivering powders into aerosol form, for example for delivering medicaments in a dry powder form.

Numerous approaches have been taken in the design and manufacture of powder delivery systems, such as dry powder delivery systems, especially since chlorofluorocarbon (CFC) gas is no longer to be used in consumer products. Some of the major disadvantages of powder delivery systems of the prior art are unintended dislodging of the powder, for example, upon dropping the inhaler, inaccurate dosage dispensing upon activation of the delivery system, and a limited number of doses or aliquots that will fit on a single delivery system. For example, many of the powder delivery systems which utilize a disc shape design are limited to the number of doses or aliquots that fit around the disc. Consequently, there is a need for a powder delivery system which is capable of attaching aliquots to a substrate until delivery of the powder is requested, and in which once activated an accurate unit dosage is then transferred from the delivery system to a treatment subject.

SUMMARY OF THE INVENTION

The disadvantages heretofore associated with the prior art are overcome by an inventive apparatuses and techniques for the enhanced release of numerous aliquots, such as doses.

The invention provides a powder delivery system comprising: a delivery system body having an internal cavity and an outlet port for delivering a powder into an aerosol form; and a rigid substrate with one or more aliquots of powder at aliquot locations on the substrate, each aliquot sealed under an individually releasable cover, wherein there is a release element for releasing each releasable cover, which release element is either (1) a mechanical release element adapted to respond to an applied force or (2) an electrical release element. In one embodiment, the powder delivery system has sufficient electrical components to provide for addressably directing voltage to release elements, wherein the application of an electrical signal to the rigid substrate delivery mechanism results in selected release of one or more of the covers.

In another embodiment, the rigid substrate is movable to align each aliquot location with a aliquot release position. In one such embodiment, the aliquot locations are arrayed along an arc and the rigid substrate is rotatable to sequentially align each of the aliquot locations with an aliquot release position.

In another embodiment, the powder delivery system has at least one vibrator that can be positioned under a aliquot location and activated to assist in releasing powder from that aliquot location.

In still another embodiment of the invention, provided is a rigid substrate for delivering powder on which multiple aliquots of powder are at aliquot locations, each aliquot sealed under an individually releasable cover, where preferably the rigid substrate has incorporated electrical release elements for releasing each releasable cover.

In still another embodiment, the invention provides a powder delivery apparatus comprising: (a) a substrate having a surface on which multiple aliquots of powder are at aliquot locations; and (b) a mechanism for displacing the substrate of the aliquot locations.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 is an illustration of a powder delivery system.

FIGS. 2A and 2B are illustrations of an aliquot contained in a rigid substrate beneath a releasable cover.

FIGS. 3A, 3B, 3C and 3D are views of releasable cover designs.

FIG. 4 is a bottom view of a powder delivery system.

FIG. 5 is a side view of a powder delivery system which reveals the prong wheel device.

FIG. 6 is a sectional view of a powder delivery system showing engagement of a prong with a substrate-traversing hole and a dosage position cover in a released position.

FIG. 7 is an illustration which displays an arrangement of the powder aliquot locations, prong holes, and dosage position covers.

FIGS. 8A and 8B are respective diagrammatic side elevation views partially in section illustrating different stages of operation of a magnetic means for releasing covers and underlying powder in the disc-type powder delivery system.

FIG. 9 illustrates a circuit board powder delivery system showing a control circuit area in relation to a mother circuit board.

FIG. 10 illustrates a circuit board assembly containing eight circuit boards.

FIG. 11 shows an example of floating electrode design.

FIG. 12 is a diagrammatic sectional elevation view of a further embodiment;

DEFINITIONS

The following terms shall have, for the purposes of this application, the meaning set forth below. In particular, for the purpose of interpreting the claims, the term definitions shall control over any assertion of a contrary meaning based on other text found herein:

Addressable

A release mechanism is addressable if the operator can either serially or selectively designate new aliquot locations on the rigid support which will be released upon the activation of a triggering device such as a button or lever.

Selected

The powder delivery system releases powder from "selected" aliquot locations if an operator can (1) select a group of one or more aliquot locations to the exclusion of other groups, or (2) the system sequentially releases the aliquots positions in a predetermined or preprogrammed manner. In either case, "selection" can with some powder delivery systems include the ability to select to release concurrently a number of aliquot locations.

Upper Surface

In referring to an "upper surface" of a substrate, Applicants intend to provide a convenient frame of reference, and not to imply that the surface must be aligned with that surface facing upwards. Similarly, other references to orientation found herein are recited to provide a convenient frame of reference.

DETAILED DESCRIPTION

An exemplary powder delivery system (such as for example an inhaler) is shown in FIG. 1. The powder delivery system has a rigid substrate delivery mechanism 1. The front section of the powder delivery system is a delivery system body 2 constructed, for example, of a plastic material and which consists of an internal cavity 3 and an outlet port 4. In one preferred embodiment a rigid substrate 5 on which is deposited powder aliquots at multiple locations is inserted into the powder delivery system through a slot with for example a snap fitting. Alternatively, in another preferred embodiment, the powder delivery system hingeably opens, revealing a fitting on which the rigid substrates can be affixed. Once the powder delivery system body 2 is connected to the rigid substrate delivery mechanism 1, the outlet port 4 is in air communication with the rigid substrate delivery mechanism 1. The outlet port 4 is illustrated as a nozzle for delivering the powder for inhalation by, for example, a treatment subject. The delivery system body also contains multiple air inlet channels 7 such that when the treatment subject inhales, air is forced through the channels 7. This combined movement of air serves a dual purpose in that its turbulence assists the release of the powder from the substrate while it also results in a velocity such that the powder is directed toward the subject for inhalation. A shuttering mechanism 8 can be provided for several of the channels 7 to control the amount of air which enters through the channels 7, which consequently can control the degree of turbulence at the internal cavity 3.

The rigid substrate 5 can contain multiple aliquots, such as doses, deposited at aliquot locations. FIG. 2 shows aliquot 10 under individually releasable cover 12 and deposited in depression cavity 13 in a rigid substrate 5. The depression cavities 13 contain the individually deposited aliquots which are preferably hermetically sealed between the covers 12 and the rigid substrate 5 by a reversibly thermosetting adhesive 15, for example wax or a hot melt adhesive, which surrounds the depression cavity 13. In addition to hermetically sealing the aliquot, the adhesive 15 holds the releasable covers against the rigid substrate preventing its release until the delivery system is activated.

In preferred embodiments, the cover 12 is formed of a material having mechanical memory, and the material is conditioned to favor a memory configuration in a shape that favors the opening of the cover 12, as illustrated in FIG. 2. This mechanical memory can be exhibited for example by a metal or plastic that is bent or formed to have a shape such as the curve of cover 12. For example, the cover can be formed with spring quality steel bent to favor the open position. In a particularly preferred embodiment, the material has a shape memory material such as a shape memory alloy which can be deformed from a memory configuration, typically with operations effected below a critical temperature (for the particular shape memory material). Such shape memory materials seek to revert to the memory configuration when heated above a phase transformation temperature. The deforming operations generally are conducted within certain guiding parameters such as a maximum strain limit that can vary with the shape memory material and the deforming process. Shape memory materials typically show a martensitic transformation that is believed to account for the shape memory effect. Temperature responsive shape memory effects can be unidirectional, for example from a position that covers an aliquot position to one that opens the aliquot position, or two way, providing for example an opening and a closing transformation. Examples of shape memory alloys include Ni—Ti, Cu—Al—Ni and Cu—Zn—Al alloys. The Ni—Ti shape memory alloys tend to show greater shape memory strain, but are costly and generally have relatively high phase transformation temperatures (such as about 250° C.). The copper-base alloys tend to provide a greater range of transformation temperatures that include relatively lower temperatures such as 90° C. Shape memory alloys are described in: T. W. Dueng, *Engineering Aspects of Shape Memory Alloys,* 1990; S. Aucken (ed.) *Progress in Shape Memory Alloys,* 1992; M. V. Gandi and B. S. Thompson, *Smart Materials and Structures*, 1992; D. E. Hodgson, *Using Shape Memory Alloys: Shape Memory Applications,* 1988. One example of a shape memory alloy, Nitinol is available from Special Metals, New Hartford, N.Y., Hitachi Metals America, Purchase, N.Y. or Dynalloy, Irving, Calif. Another example, Tinel™ is available from Raychem, Menlo Park, Calif.

In an embodiment, FIG. 2A, where the releasable covers 12 are formed of a material having a mechanical memory, during assembly the releasable cover is forced down against the rigid substrate and an adhesive 15 (such as a reversibly thermosetting adhesive) holds the cover down to protect the aliquot during storage. Activation of either a stepper mechanism type powder dispenser or a circuit board type powder dispenser will allow the covers to seek the memory configuration and uncover the corresponding aliquot. In another embodiment, FIG. 2B, the releasable covers 12' are made of a shape memory alloy, such as Nitinol, such that when a current is selectively applied to the cover it via contacts 67 and conductor 69 as the aliquot is moved into position, the current heats the alloy causing it to return to the memory configuration and pull away from the adhesive 15 as shown in phantom.

FIG. 3A shows an embodiment where heat for activating a transition, such as a heat-initiated change of shape or a heat-initiated loss of adhesion is provided by leads 17A and 17B, which serve as resistors in a circuit that includes cover 12 (the leads and the cover can be considered one shape-transitioning unit). FIG. 3B shows a perspective view of this embodiment. When current is applied, for instance in the directions indicated by the arrows in FIG. 3A, the heat developed at the leads 17A and 17B acts to loosen adhesive that retains the leads 17A and 17B or to initiate a temperature-initiated shape transition, leading to the leads 17A and 17B lifting off the substrate 5, as indicated in FIG. 3C. Where an inhaler is designed to promote gas flow across the rigid substrate 5, for example in the direction indicated by arrow W, turbulence created in the space above the cavity 13, which is enhanced by the heating at leads 17A and 17B. This turbulence enhances the release of an aliquot of material stored in cavity 13. FIG. 3D shows an alternative embodiment in which the substrate has heating elements 14 (such as resisters, such as a film of resistor material, for example a thick film resistor) embedded underneath the cover 12 (not shown here), in an area surrounding the cavity 13, for providing the heat which releases the cover 12.

In one embodiment of the invention, the rigid substrate 18 has aliquot positions arrayed in an arc (which can be a circle or spiral), such as on the disk substrate 18 shown in FIG. 4. Prong holes 20 are adjacent to each aliquot such that as the disc is manually rotated to the next position, prong wheel 21 teeth 25, FIG. 5, move from one hole to the next hole. The prong wheel is mounted on and can slide on a shaft axle 23 mounted so that the sprocket can move towards the center of the disc to follow the spiral (not shown). When a prong tooth slides into a substrate-traversing hole, the tooth pushes the releasable cover upward to break the seal and expose the powder. For example, in the illustration of FIG. 4, the substrate 18 constructed of, for example, plastic material, has a radial track 19 of substrate-traversing holes 20. A prong wheel 21 is mounted on an axle 23 such that the prong wheel follows the course of the circumferential track as the prongs 25 progress through the substrate-traversing holes 20. In one preferred embodiment, the prong wheel is rotated by a mechanical stepper mechanism 66, and in another the prong wheel is rotated with an electrical mechanism (not shown). The prong wheel 21 is mounted on axle 23, which in turn is mounted in axle mounts 22. In for example an embodiment where the substrate-traversing holes are arrayed in a spiral (not shown), the prong wheel can be slidably mounted on the axle so that the prong wheel can move laterally along the path defined by the spiral.

Figure 5:
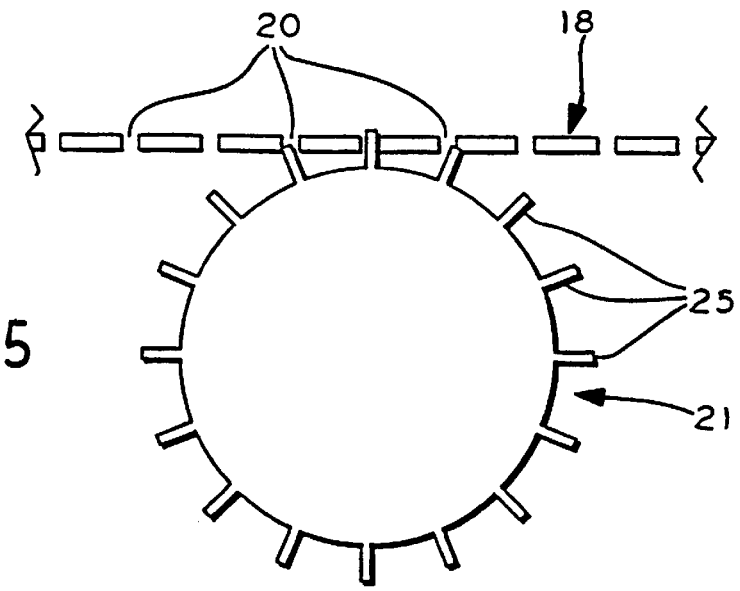

FIG. 5 shows the prong wheel 21 in relation to the substrate 18. One prong 25 is fully engaged with a substrate-traversing hole 20, while the remaining prongs 25 are only partially or not at all engaged with substrate-traversing holes 20. The prong wheel is preferably rotated by a mechanical or electromechanical stepper mechanism (not shown). In preferred embodiments, a defined number of activations of the stepper advances an aliquot location to a release position.

Figure 6:
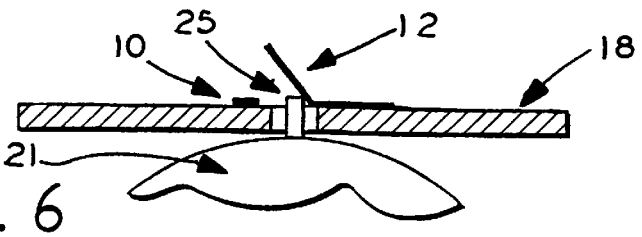
Figure 7:
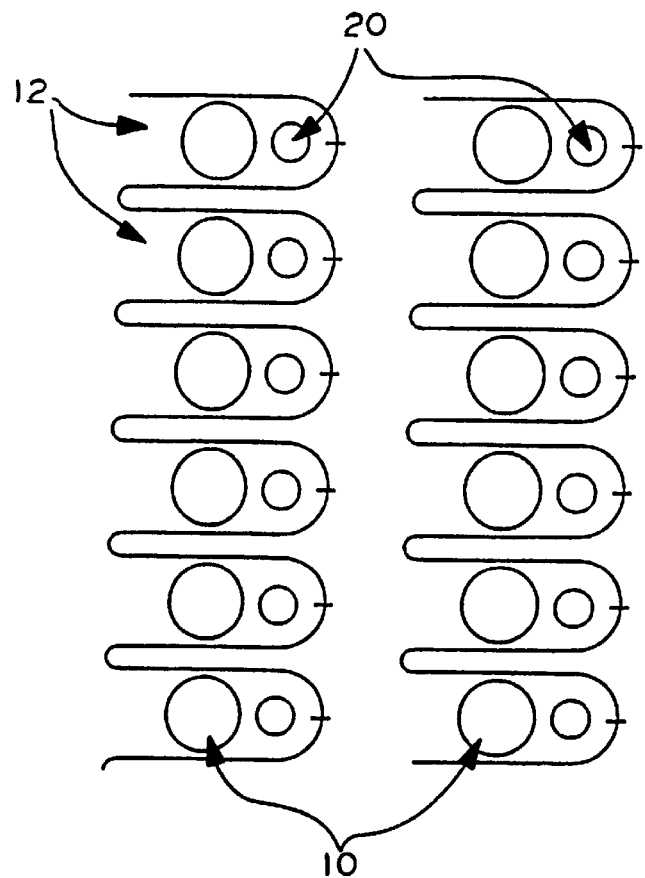
Figure 8B:
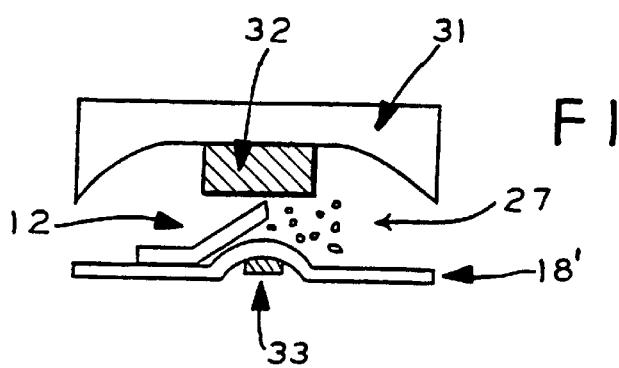
Figure 8A:
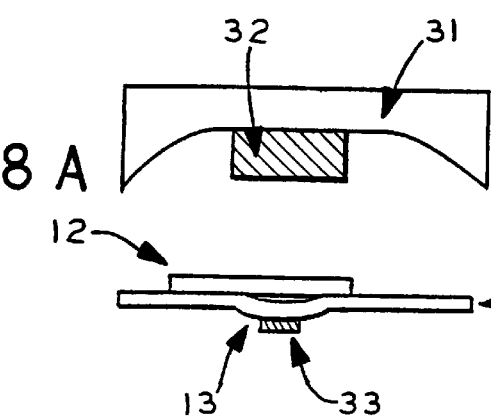
Figure 9:
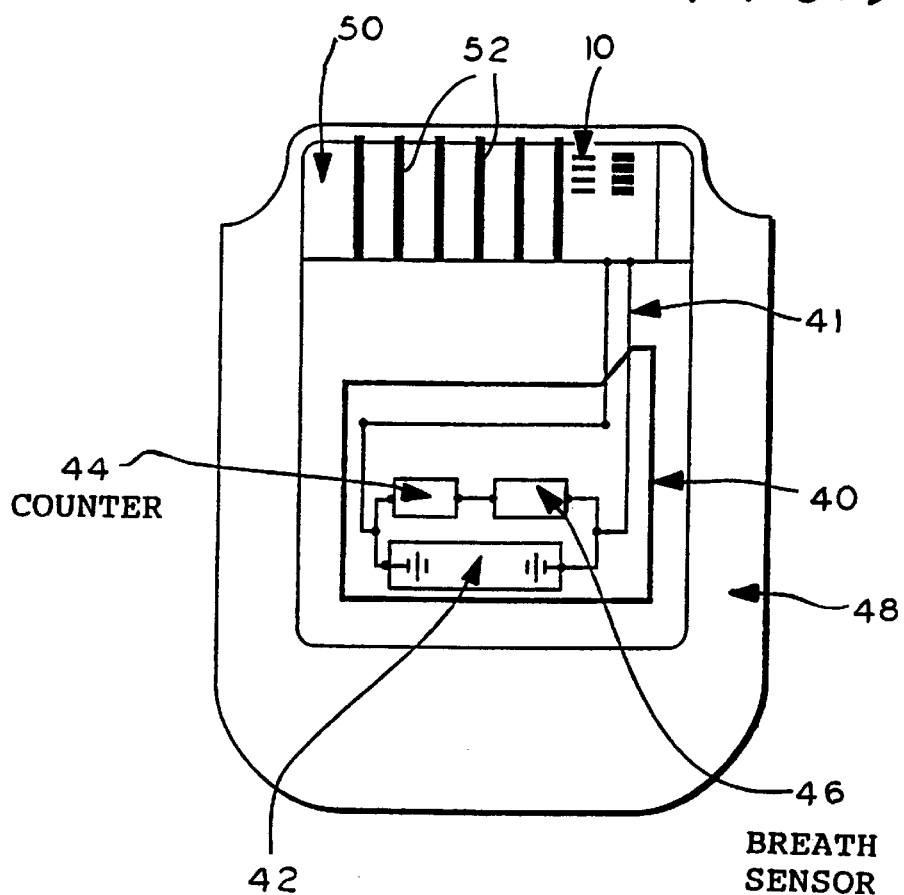
Figure 10:
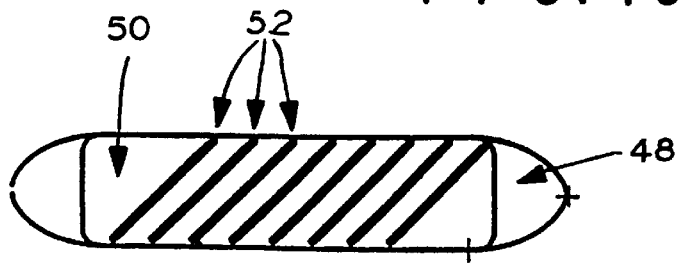

FIG. 6 shows that when a prong 25 on a prong wheel 21 is aligned with a substrate-traversing hole it comes in contact with a releasable cover 12 thereby releasing it from the rigid substrate 18 and exposing the underlying aliquot 10. FIG. 7 shows the proximity of the aliquots 10 to the substrate-traversing holes 20. Two series of six dosage locations are shown in FIG. 7. The prong, while illustrated here as moved by a simple gear mechanism, can of course be moved with more sophisticated gearing, for instance incorporating cams that accentuate the substrate traversing movement of the cam, or with an escapement mechanism that indexes with successive activations, which activations can for example be mediated with a button.

Analogously to the powder delivery system having substrate-traversing holes, electrical release elements can also be driven by mechanical motion of the rigid substrate or a release probe. The release probe can be made up of one or more electrical leads for contacting complementary leads on the rigid substrate.

In another embodiment, the rigid substrate 18' reversibly snaps between a concave and a convex shape, as illustrated in FIGS. 8A and 8B, respectively. In FIGS. 8A and 8B, a magnet 32 (such as a rare earth magnet) held by magnet support 31 is used to effect this transition. Where the substrate is not itself sufficiently magnetically susceptible to respond to the magnet, a magnetically permeable material 33 (such as a ferrous material) can be placed under the substrate 18' as illustrated. The snap transition of the substrate 18 causes a displacement of the cover 12 and release of powder 27. The magnet can be moved into sufficient proximity to achieve the critical magnetic force needed to initiate the snap transition, or a programmed movement of the substrate can bring an aliquot position within sufficient proximity to the magnet. Alternatively, a prong can be used to initiate the transition. The snap transition applies momentum to the powder and helps deliver an aerosol.

In preferred embodiments, the powder delivery system utilizes no moving parts such as spools, gears, lever, ratchets, tapes, discs, etc. but rather is based on printed circuit board technology. As FIG. 9 illustrates, a circuit board delivery system with addressing circuitry 41, battery 42, counter 44, breath sensor 46, and protective housing 48. The circuit board powder delivery system utilizes the control circuitry area 40 to individually address each aliquot 10 on the mother circuit board 50. The control circuit area 40 is adjacent and electrically connected to the mother circuit board 50 which contains bands of smaller circuit boards 52, each circuit board 52 containing for example forty-two (42) aliquots 10 and capable of being plugged into the mother circuit board 50 in any combination. In addition, the mother circuit board 50 can be arranged in many combination patterns including, for example, a single board, multiple boards, single or double sided boards, flexible or rigid boards.

By way of example, FIG. 9 shows a front view of the mother circuit board 50 with six (6) small boards 52 each with forty-two (42) aliquots (not shown) plugged into the mother circuit board 50. In one embodiment, the circuit boards 52 are installed at an angle (FIG. 10) to the mother circuit board 50 which enables the circuit boards to be longer and therefore contain more powder aliquots on a single circuit board 52. With this arrangement, a vendor, for example, could stock a supply of circuit board delivery systems without powder and a supply of powder drug circuit boards with various powders contained on them. In a pharmaceutical context, a prescription may call for eighty-four (84) doses of drug "A". The pharmacist could then supply two forty-two (42) dose circuit boards of drug "A", which can then be plugged into the powder delivery system.

The circuit board embodiments are embodiments where the powder delivery system includes in the rigid substrate a substantial portion of the electrical components needed to address a release-initiating voltage to an appropriate aliquot location. The applied signal can contain the address of the electrical release elements and thus direct where the releasing voltage will be directed, or the application of an electrical signal with less information content can advance an internal counter that designates to which release elements voltage is directed.

The rigid substrate can be made of any number of materials suitable for holding the powder intended to be deposited thereon, which materials can include glass, porcelain, silicon, plastic, and the like. While the discussion herein refers to the substrate as rigid, this does not mean inflexible, it means sufficiently rigid as to be readily handled as a solid instead of, by way of example, a flexible film such as a film suitable for photography.

In preferred embodiments of the invention, the powder is deposited by electrostatic deposition or controlled field deposition. In electrostatic deposition methods a substrate is sufficiently electrically isolated so that an electrostatic charge can be accumulated on the substrate. One means of accumulating the charge is by taking advantage of the photoelectric effect. In this method the substrate is exposed to electromagnetic radiation effective to strip charges, typically electrons, from the surface of the substrate. Other methods include tribocharging and plasma treatment. In a more preferred method, an ion emitter is oriented towards the surface on which one intends to create a charge and operated. Such methods of ion printing to controllably electrostatically deposit charged materials such as powders are described in detail in U.S. application Ser. Nos. 08/471,889 (filed Jun. 6, 1995), now U.S. Pat. No. 5,714,007, 08/659,501 (filed Jun. 6, 1996) and 08/733,525 (filed Oct. 18, 1996), which documents are incorporated by reference herein in their entirety.

It should be noted that for a given deposition material where the average charge-to-mass ratio of the charged particles of the deposition material is known, the mass of particles that will effectively deposit can be relatively accurately predicted from the amount of charge previously accumulated on the substrate. In particular, for a given type of substrate and deposition material a calibration database can be compiled. In a production protocol, the average charge-to-mass ratio of the particles can be monitored, for instance using the velocimeter and a modified quartz crystal monitor (not shown). With the use of one or more charge to mass monitors, feedback loops can be incorporated into the electrical controls of a deposition apparatus. In one preferred embodiment, a charge-to-mass monitor is positioned so as to sample the charge-to-mass of particles at their source (examples for source devices described below) and another is positioned adjacent to the site of deposition. The sampling values produced at these two sites provide diagnostic data on the operation of the deposition apparatus.

A variety of additional factors can be monitored or controlled to increase the reproducibility of the charge-to-mass ratios generated by the charged deposition material source. For example, the humidity of the local environment and the type and quantity of bound solvent in the materials sought to be deposited can be important.

Another method of attracting charged deposition materials to a surface has been termed "controlled field deposition," and typically involves applying a potential to an electrode which directly or indirectly results in the formation of an attractive electrical field at the surface upon which charged material will be deposited. For example, a substrate can have electrical conductors positioned below the deposition surfaces, and a potential applied to the conductors results in the formation of an attractive field at the surface. Where the separation between the substrate's surface and the conductors is sufficiently small, once an external potential is no longer applied to the conductors the charge of deposited material results in a charge redistribution in the conductors such that an electrostatic "image" force is formed between the deposition material and the conductors, thereby helping to stabilize the deposition material's adherence to the surface.

Figure 11:
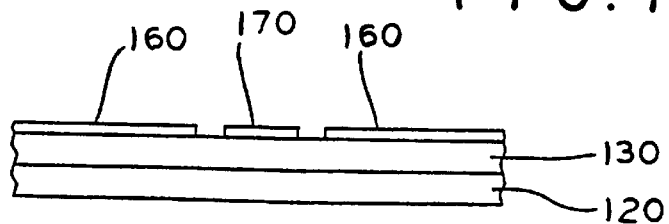

Further examples of field-generating means include the use of "floating electrodes." A floating electrode is an electrode which develops a localized field as a result of charge redistributions in the floating electrode, which are for example generated by voltages applied across adjacent bias electrodes. Thus, for example, as illustrated in FIG. 11, a floating electrode apparatus can have a backing electrode 120, a non-conductive layer 130, a shielding electrode 160 and a floating electrode 170. In the illustrative floating electrode, a bias potential applied across the backing electrode and the shielding electrode (which two electrodes serve as the bias electrodes) causes a charge redistribution in the floating electrode to create the charged-particle attracting field at the floating electrode. Further description of floating electrodes and other forms of field generating devices for controlled field deposition can be found in U.S. application Ser. No. 08/661,210, filed Jun. 10, 1996, which document is incorporated herein by reference in its entirety. An advantage of floating electrode devices is that the amount of charged particles that will effectively adhere as a result of the field generated at the floating electrode depends on the size of the bias potential. (For more direct field generating apparatuses, the deposition can in principle continue for as long as a potential is applied.)

The field generating devices for controlled field deposition can be designed (a) to directly apply deposition material onto apparatuses that incorporate electrodes for generating the field or (b) for use with electrostatic chucks which operate in conjunction with the substrate on which deposition material is to be applied. In the former case (a), it is generally desirable that the metallization processes used to create the electrodes is susceptible to mass production techniques. For example, the metallization can be created by lithographic techniques where finely patterned electrodes are sought or by adhering or fusing metal layers to the substrate. In design (b), the electrostatic chuck is generally effective to electrostatically adhere the substrate to the chuck. This adherence of the substrate does not necessarily depend on the application of any process for creating a charge on the substrate, but instead is believed to be the result of a redistribution of charges in the substrate in response to the field generated by the electrostatic chuck. A third option is that the substrate is designed to reversibly couple with a device that provides the electrodes, such that the substrate and the coupled device provide a field-generating apparatus. In this way, the electrode structures that can be a source of manufacturing costs remain separate from the consumable on which reagents for conducting a chemical process will be deposited. In addition to the documents recited above, further information on electrode structures and electrostatic chucks can be found in U.S. application Ser. No. 08/630,012, filed Apr. 9, 1996, now U.S. Pat. No. 5,788,814 which document is incorporated herein by reference in its entirety.

The charge of the particles applied to a substrate can be generated for example by plasma treatment, radiation treatment (including treatment with suitably high energy electromagnetic radiation) or ion bombardment. More preferably, however, the charge is generated by tribocharging, wherein two materials with differing triboelectric constants rub against each other and transfer charge between one another. Tribocharging is more preferred over the enumerated charge-producing methods because it exposes the particles to the least amount of reaction-promoting energy, and hence the tribocharging method is less susceptible to causing compounds to degrade. Examples of materials that can be used for tribocharging include polytetrafluoroethylene ("TEFLON"), and polymers of chlorotrifluoroethylene, chlorinated propylene, vinyl chloride, chlorinated ether, 4-chlorostyrene, 4-chloromethoxystyrene, sulfone, epichlorhydrin, styrene, ethylene, carbonate, ethylene vinyl acetate, methyl methacrylate, vinyl acetate, vinyl butyral, 2-vinyl pyridine styrene, nylon and ethylene oxide. See, for example, "Triboelectrification of Polymers" in K. C. Frisch and A. Patsis, *Electrical Properties of Polymers* (Technomic Publications, Westport, Conn.), which article is hereby incorporated by reference in its entirety. For example, polytetrafluoroethylene and polyethylene and other negatively charged materials will generally create a positive charge on an object. Nylon and other positively charged materials will generally create a negative charge on an object. Tribocharging and appliances for dispensing charged particles are describe in U.S. application Ser. Nos. 08/659,501 (filed Jun. 6, 1996) now U.S. Pat. No. 5,753,302 and 08/661,211 (filed Jun. 10, 1996). U.S. application Ser. No. 08/661,211 describes, in particular, an acoustic dispenser that uses vibratory energy and gating electric fields to dispense charged particles for deposition onto the substrate, and is incorporated herein by reference in its entirety.

In some embodiments, the charged particles may be made up of a wet toner wherein particles of liquid material or liquid material with suspended solids are charged. Charging of the liquid particles can be by, for example, tribocharging occurring at the time the particles are formed. Often it is favorable to dry deposit materials to avoid issues of solubility and stability of a chemical. On the other hand, however, liquid phase depositions are often practical, especially where, when appropriate, cautionary procedures, such as limiting the time of exposure to the liquid phase and selecting appropriate carrier solvents, are employed.

Where the aliquot locations are arrayed on an upper non-conducting surface of the rigid substrate and the powder delivery system further comprises one or more strips of conductive material applied to a lower surface of the rigid substrate, in a preferred embodiment the upper non-conductive surface at the aliquot locations is textured, with the dimensions of the texture selected so as to reduce the tendency of powder particles to adhere to the substrate. Such dimensions limit the surface area of the particles that is adjacent to a smooth substrate surface. In another preferred embodiment, for each aliquot location on the rigid substrate conductive material is found on the corresponding lower surface of the rigid substrate and is effective to create an image force tending to adhere any charged particles positioned at the aliquot locations.

Such conductive surfaces located adjacent to the charged powder can also be used to assist in release by applying a voltage of the appropriate polarity to these conductive surfaces. In certain embodiments, the release voltage can be applied non-selectively, since covers will prevent release of powder that is not found at an appropriate aliquot location. In other embodiments, selective electrical pathways will parallel those used to deliver voltages for opening the appropriate aliquot locations.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A powder delivery system comprising:

a body having an internal cavity and an outlet port for delivering a powder into an aerosol form;

a substrate with one or more aliquots of powder, each aliquot at an aliquot location on the substrate, each aliquot sealed under an individually releasable cover; and an electrical release element for electrically releasing each releasable cover, the substrate having electrical conductors for selectively applying voltage to the electrical release element to thereby selectively release the corresponding cover.

2. The powder delivery system of claim 1, further including a plurality of aliquots, corresponding covers and corresponding release elements and further comprising a plurality of electrical components for selectively addressably directing voltage to the electrical release elements, wherein the application of an electrical signal to the selected release elements results in selected release of the corresponding covers.

3. The powder delivery system of claim 1, including means for moving the substrate to align each aliquot to a release position, wherein when the substrate is moved to align an aliquot with its aliquot release position, electrical contacts are made that direct voltage to a selected electrical release element.

4. The powder delivery system of claim 1, wherein:

either (a) the releasable cover is secured by a reversibly thermosetting adhesive, or (b) the releasable cover is formed of a material having mechanical memory and is conditioned to favor a memory configuration, wherein, when secured to the substrate the cover in the closed condition is bent out of the memory configuration, or (c) both (a) and (b) apply.

5. The powder delivery system of claim 4, wherein the material having mechanical memory is a shape memory material that adopts its memory configuration when heated to a memory temperature.

6. The powder delivery system of claim 1, including a plurality of aliquot locations, the substrate having an upper electrically non-conductive surface and a lower surface wherein the aliquot locations are arrayed on the upper non-conducting surface of the substrate and further comprising a strip of conductive material applied to the lower surface of the substrate at each location.

7. The powder delivery system of claim 6, further comprising a voltage source for applying a powder release-assisting voltage to one or more of the strips of conductive material.

8. A substrate for delivering powder on which multiple aliquots of powder are at corresponding aliquot locations, each aliquot sealed under an individually releasable cover, the substrate including a plurality of electrical release elements, each element corresponding to a separate aliquot cover, each release element for releasing the corresponding cover.

9. The substrate of claim 8, wherein:

the release elements comprise a plurality of electrical pathways, each pathway corresponding to a different cover for selectively applying a received voltage to each electrical release element to thereby selectively release the covers.

10. The substrate of claim 8 wherein the covers are formed of a material having mechanical memory and are conditioned to favor a memory configuration, wherein, when covering a aliquot location each cover is out of the favored memory configuration, and wherein activation, for any aliquot location of the electrical release element for that aliquot location sufficiently releases the corresponding cover to allow it to seek the favored memory configuration and uncover an aliquot of powder.

11. A powder delivery system comprising:

a body having an internal cavity and an outlet port for delivering a powder into an aerosol form;

a substrate in the cavity with at least one aliquot of powder at a corresponding aliquot location on the substrate, the at least one aliquot being sealed under a corresponding separate, discrete individually releasable cover in a cover closed position, the cover having memory and favoring a predetermined memory configuration; and means for selectively causing the cover to displace to a cover open favored memory configuration.

12. The powder delivery system of claim 11, wherein the means for selectively causing comprises at least one hole passing through the substrate, a mechanism for inserting a prong into the at least one hole, wherein the insertion of the prong into the at least one hole deflects the cover at an aliquot location causing the cover to adopt the memory configuration.

13. The system of claim 11 wherein the cover has a memory in a bent condition that favors the open position and the means for causing including means for retaining the cover closed against the force of the bent favored open position and including means for releasing the retaining means.

14. The system of claim 13 wherein the means for retaining comprises a reversibly thermosetting adhesive.

15. The system of claim 13 wherein the means for releasing comprises mechanical means coupled to the body for applying a displacement force to the cover.

16. The system of claim 11 wherein the cover has a first memory configuration in the closed position at a first temperature and a second memory configuration in the open configuration at a second temperature higher than the first temperature, the means for causing including means placing the cover at the second temperature.

17. The system of claim 16 wherein the means for placing includes electrical means for electrically heating the cover.

18. The system of claim 16 wherein the cover includes leads that have a first position at the first temperature and a second position at the second temperature, the leads for opening the cover when heated to the second temperature in response to an applied electrical signal.

19. A powder delivery system comprising:
   a body having an internal cavity and an outlet port for delivering a powder into an aerosol form;
   a substrate in the cavity with at least one aliquot of powder at a corresponding aliquot location on the substrate, the at least one aliquot being sealed under an individually releasable cover in a cover closed position;
   an aliquot cover having an aliquot closed position and an open position; and
   a cover release mechanism comprising an electrical release element responsive to an applied electrical signal for electrically releasing the cover.

20. A powder delivery system comprising:
   a body having an internal cavity and an outlet port for delivering a powder into an aerosol form;
   a substrate with one or more aliquots of powder, each aliquot at an aliquot location on the substrate, each aliquot sealed under an individually releasable cover, an electrical release element for electrically releasing each releasable cover; and
   means for moving the substrate to align each aliquot to a release position, wherein when the substrate is moved to align an aliquot with its aliquot release position, electrical contacts are made that direct voltage to a selected electrical release element.

21. A powder delivery system comprising:
   a body having an internal cavity and an outlet port for delivering a powder into an aerosol form;
   a substrate with one or more aliquots of powder, each aliquot at an aliquot location on the substrate, each aliquot sealed under an individually releasable cover; and
   an electrical release element for electrically releasing each releasable cover, the cover having a memory configuration in a cover open position including means for causing the closed cover to assume the cover open position from the sealed condition for each releasable cover, the cover material having a memory configuration comprising shape memory material that adopts its memory configuration when heated to a memory configuration.

22. A powder delivery system comprising:
   a body having an internal cavity and an outlet port for delivering a powder into an aerosol form;
   a substrate with one or more aliquots of powder, each aliquot at an aliquot location on the substrate, each aliquot sealed under an individually releasable cover, and
   an electrical release element for electrically releasing each releasable cover and the corresponding aliquot of powder.

23. A powder delivery system comprising:
   a body having an internal cavity and an outlet port for delivering a powder into an aerosol form;
   a substrate with a plurality of aliquots of powder, each aliquot at a separate discrete aliquot location on the substrate, each aliquot sealed under an individually releasable cover; and
   an electrical release element for electrically releasing each releasable cover;
   the substrate having an upper electrically non-conductive surface and a lower surface wherein the aliquot locations are arrayed on the upper non-conducting surface of the substrate and further comprising a strip of conductive material applied to the lower surface of the substrate at each location.

* * * * *